United States Patent [19]

Ohkuwa

[11] Patent Number: 4,747,661
[45] Date of Patent: May 31, 1988

[54] ENDOSCOPE TIP ADAPTOR

[75] Inventor: Hideki Ohkuwa, Hachioji, Japan

[73] Assignee: Olympus Optical Co., Ltd., Tokyo, Japan

[21] Appl. No.: 47,390

[22] Filed: May 8, 1987

[30] Foreign Application Priority Data

May 15, 1986 [JP] Japan ............................. 61-73387[U]

[51] Int. Cl.⁴ ............................................. G02B 23/26
[52] U.S. Cl. .............................. 350/96.26; 350/96.22
[58] Field of Search ............... 350/96.25, 96.26, 96.22, 350/96.20; 356/241

[56] References Cited

U.S. PATENT DOCUMENTS

| | | | |
|---|---|---|---|
| 3,818,902 | 6/1974 | Kinoshita et al. | 350/96.26 X |
| 4,195,904 | 4/1980 | Yamashita | 350/68 |
| 4,279,465 | 7/1981 | Vojvodich | 350/96.20 |
| 4,500,181 | 2/1985 | Takahashi | 350/96.26 X |
| 4,558,691 | 12/1985 | Okada | 350/96.26 X |
| 4,576,147 | 3/1986 | Hashiguchi | 350/96.26 X |
| 4,653,848 | 3/1987 | Kloots | 350/96.22 |

FOREIGN PATENT DOCUMENTS 56-70744 6/1981 Japan .
56-85324 7/1981 Japan .

*Primary Examiner*—John Lee
*Assistant Examiner*—Phan Heartney
*Attorney, Agent, or Firm*—Armstrong, Nikaido, Marmelstein & Kubovcik

[57] ABSTRACT

The endoscope tip adaptor has an objective optical system capable of varying the observing direction with respect to the optical axis of an endoscope side optical system and a light guide of an optical axis inclined with the optical axis of an endoscope side light guide, is to be removably fitted to an endoscope tip surface, secures a space so that the light guide may not be broken and expands the range which can be observed.

7 Claims, 3 Drawing Sheets

ENDOSCOPE TIP ADAPTOR

FIELD OF THE INVENTION

This invention relates to an endoscope tip adaptor fitted to the tip part of an endoscope and having a light guide arranged in a direction inclined from the axial direction of the light guide on the endoscope side.

BACKGROUND OF THE INVENTION

Recently, there has come to be extensively used an endoscope whereby an elongate insertable part can be inserted into a body cavity to observe or diagnose an internal organ or the like within the body cavity without incising it or to cure it by using a treatment tool.

In case the insertable part of the above mentioned endoscope is inserted into a body cavity to observe an affected part or the like, if the affected part is in the forward direction of the axis of the tip side of the insertable part, it will be easy to observe the affected part with a straight sight type endoscope. On the other hand, in case an inner wall surface of a body cavity on the side intersecting at right angles with the inserting direction is to be observed, it will be easy to observe such inner wall surface with a side sight type endoscope. It is desirable to use endoscopes adapted to these positions to be observed. However, the endoscope is so expensive that, in the prior art example disclosed, for example, in Japanese Patent Laid Open Nos. 70744/1981 and 85324/1981, an adaptor provided with an optical system different in the visual field direction or the like is fitted to the tip of the insertable part of an endoscope to be used so that the observation may be made in a different visual field direction or different angle of vision.

In the above mentioned prior art example, such illuminating light transmitting means as a prism or light guide is used. For example, in case an adaptor is fitted to the tip of a straight sight type endoscope so that a side sight direction may be observed, a light guide arranged within to transmit an illuminating light will be higher in the illuminating light transmitting efficiency than a prism arranged within and therefore it will be desirable to use a light guide. In case a light guide is used, it will have to be bent. In the above mentioned prior art example, the entrance end surface of the light guide on the adaptor side is connected to the exit end surface of the light guide on the endoscope side so that the axial directions of both light guides in their connecting part may coincide with each other and, on the forward side of this part, the light guide within the adaptor is arranged as bent substantially by 90 degrees.

It is disclosed in U.S. Pat. No. 4,195,904 that an adaptor having an optical system which can vary the illuminating and observing directions is provided in the tip part of an endoscope.

However, there has been a defect that, in the connection and arrangement of the light guide in the above mentioned prior art example, the radius of curvature of the light guide is so small that the light guide is likely to be broken. Also, there has been a defect that, in fitting a straight sight type endoscope with a straight sight type adaptor for varying the angle of vision, the positions of arranging the observing optical system and illuminating optical system within the adaptor are likely to interfere with each other, only small optical systems can be arranged and therefore it is difficult to secure a sufficient resolving power.

OBJECTS AND SUMMARY OF THE INVENTION

An object of the present invention is to provide. an ensosocpe tip adaptor which can be arranged so as not to break the light guide and so as to be able to well secure the optical system containing space.

Another object of the present invention is to provide an endoscope tip adaptor wherein the space for both illuminating and observing optical systems arranged within is secured, the radius of curvature in case the light guide is bent is so large as to reduce breaking of the light guide and the space for containing an optical system for varying the angle of vision is secured.

In the present invention, an adaptor side light guide to be connected to an endoscope side light guide is provided in an adaptor provided on the tip surface of an endoscope and is arranged in an oblique direction deviating from the extension of the axis of the above mentioned endoscope side light guide.

The other features and advantages of the present invention will become apparent enough with the following explanation.

DETAILED DESCRIPTION OF THE PREFERRED EMBODIMENTS

The present invention shall be explained in detail in the following with reference to the drawings.

Figure 1:
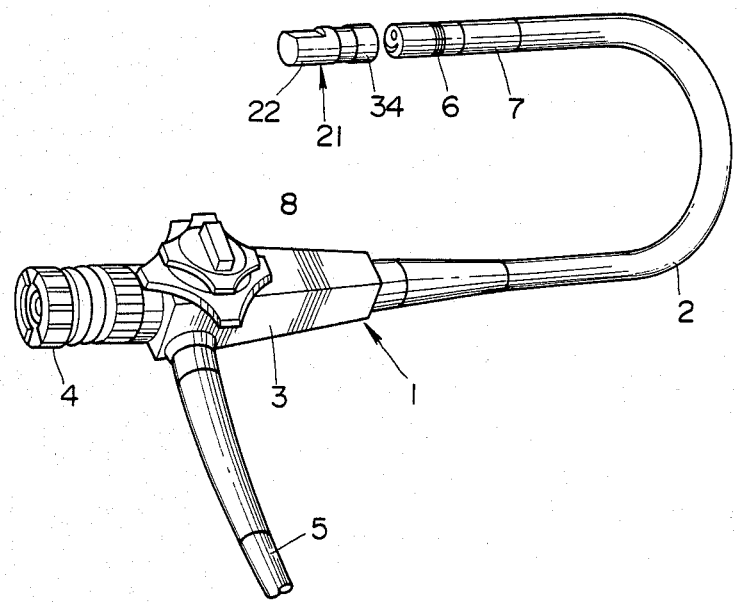
FIG. 1 is a perspective view showing an endoscope to be fitted with the first embodiment.

As shown in FIG. 1, an endoscope 1 to be fitted with the first embodiment is formed of an elongate flexible insertable part 2, a wide operating part 3 provided as connected to the rear end side of this insertable part 2, an eyepiece part 4 formed at the rear end of this operating part 3 and a light guide cable 5 provided to project on the side of the operating part 3. A tip part 6 containing an optical system is formed at the front end of the above mentioned insertable part 2. A curvable part 7 is formed in the rear end part adjacent to this tip part 6 so as to be curvable vertically or horizontally by rotating an angle knob 8 of the operating part 3.

Figure 2:
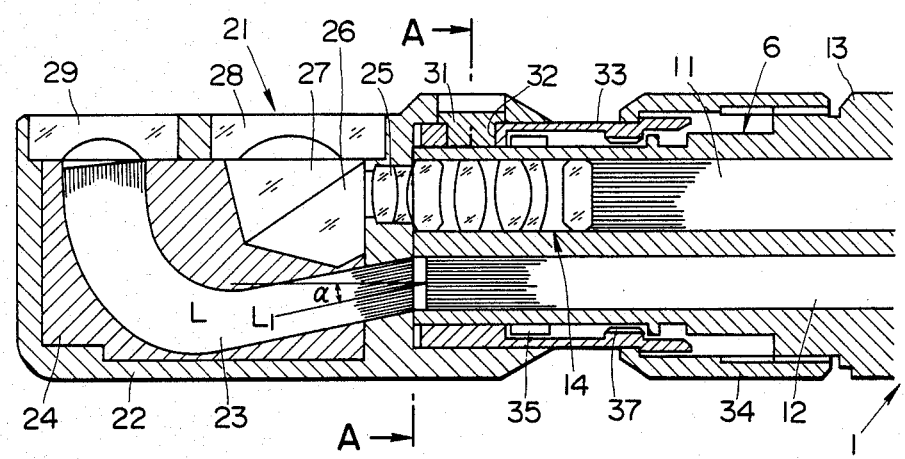
FIG. 2 is a sectioned view showing the structure of the first embodiment as fitted to the endoscope.

As shown in FIG. 2, an image guide 11 as an image transmitting means and a light guide 12 as an illuminating light transmitting means are inserted through the above mentioned insertable part 2. As shown in FIG. 2, this image guide 11 is fixed at the front end with a through hole within a tip part body 13 of the tip part 6 so that an image may be formed on the front end surface of this image guide 11 by an objective system 14 arranged in the front part. The image formed on this front end surface is transmitted to the rear end surface of the image guide 11 and can be magnified and observed from the rear of the eyepiece part 4 through an eyepiece not illustrated. The light guide 12 inserted through the insertable part 2 adjacently to this image guide 11 is secured on the tip side with the through hole within the tip part body 13, is adjacent on the front end surface to a window part of the objective system 14 and is exposed out at the exit end to be an illuminating window.

Figure 3:
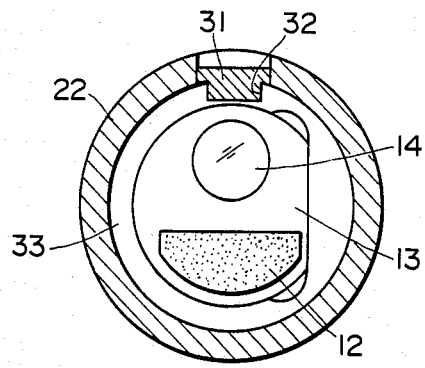
FIG. 3 is a sectioned view on line A-A in FIG. 2.

As shown in FIG. 3, the exit end surface of this light guide 12 is substantially semi-circular. There is formed the straight sight type endoscope 1 wherein an illuminating light is projected forward in the axial direction of the insertable part 2 out of the exit end surface of this light guide 12 and an illuminated forward object is imaged to be observable by the objective system adjacent to the exit end surface of this light guide.

An endoscope tip adaptor 21 of the first embodiment can be removably fitted to the tip part 6 of the insertable part 2 of this endoscope 1.

In this (endoscope) tip adaptor 21, a light guide 23 by a curved fiber bundle as inserted through a curved through hole of a fixing member 24 is fixed to an adaptor body 22 provided with a recess on the side. The entrance end (rear end) of the light guide 23 fixed as inserted through this through hole substantially overlaps the exit end of the light guide 12 but is so arranged as to be directed in an oblique direction $L_1$ forming a proper angle $\alpha$ with the extension L of the center axis of the light guide 12 on the endoscope side. This oblique direction $L_1$ is on the side reverse to the side opposed to the objective system 14. A visual field varying optical system is arranged in the part opposed to the objective system 14 and having a space secured by the arrangement in this oblique direction $L_1$.

That is to say, in the part opposed to the objective system 14, an optical lens 25 and light path varying prisms 26 and 27 are secured to the adaptor body 22 and fixing member 24 and the prism 27 having the entrance surface on the side is further closed with a lens 28 which has a concave formed and is also a cover glass to form an observing optical system with which the side can be observed.

The light guide 23 arranged adjacently to this visual field varying observing optical system is curved with a comparatively large radius R of curvature (See FIG. 4) on the forward side from the light entrance end so that the exit end surface may be on the side observable with the above mentioned observing optical system. This exit end surface is also closed with a light distributing lens 29 having also a function as of a cover glass.

Now, on the rear end base side of the adaptor body 22 forming this tip adaptor 21, a recess is formed, a pin 31 is provided to project in the inward direction in this recess and a substantially cylindrical joint (member) 33 in which a groove 32 capable of containing this pin 31 is formed is secured. The inside shape of this joint 33 is so made as to fit the tip part 6 of a shape incised on one side (See FIG. 3). A female screw 37 formed on the inner wall of the cylindrical joint 33 and a male screw 35 formed on the outer periphery of the tip part 6 are to be screwed with each other.

When the cylindrical joint 33 is rotated, the female screw 37 and male screw 35 will be screwed with each other but, when it is further rotated, the screws will be disengaged with each other, the rotating positions of the tip part 6 and cylindrical joint 33 will be regulated by the incisions of the tip part 6 and cylindrical joint 33 and the optical system of the tip adaptor 21 and the optical system on the endoscope side will be opposed to each other.

Then, when a connecting ring 34 is rotated, a female screw of the connecting ring 34 and a male screw of the tip part body 13 will be screwed with each other and the tip adaptor 21 and the tip part 6 will come to optically predetermined positions.

Here, even if the connecting ring 34 is disengaged, the female screw 37 of the cylindrical joint 33 and the male screw 35 of the tip part 6 will engage with each other and a drop preventing mechanism will act on the tip adaptor 21.

It shall be explained in the following with reference to FIG. 4 that the light guide 23 arranged within the above mentioned tip adaptor 21 extends in the oblique direction from the extension of the endoscope side light guide 12 and, by bending the forward side of the extended part, the radius of curvature can be made larger than on the extension.

Figure 4:
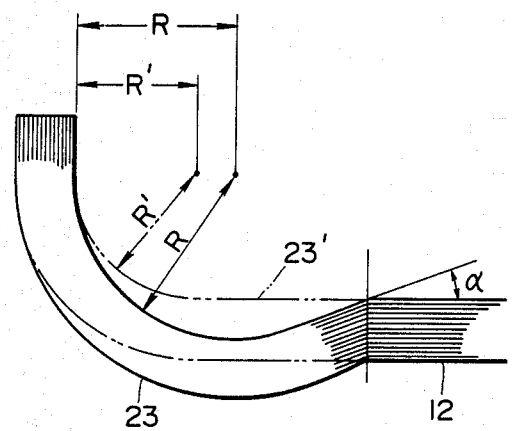
FIG. 4 is an explanatory view showing a light guide arranged as bent with a large radius of curvature in the first embodiment.

In FIG. 4, in case a light guide 23' provided on the extension of the light guide 12 of the endoscope is bent, the (inside) radius of curvature will be R'. On the other hand, in case the light guide 23 of the first embodiment inclined in the direction forming an angle $\alpha$ with the endoscope side light guide 12 is bent, the (inside) radius of curvature will be R. This radius R of curvature can be made larger than R'. Therefore, with the larger radius R of curvature, the fiber can be prevented from being broken in case it is arranged as bent and can be reduced in the accident of being broken by the impact in case it is operated. Also, by extending and providing the light guide in this oblique direction, the observing optical system containing space can be made wider, the total length of the adaptor can be made shorter and the pain of the patient in case the adaptor is inserted can be reduced.

Figure 5:
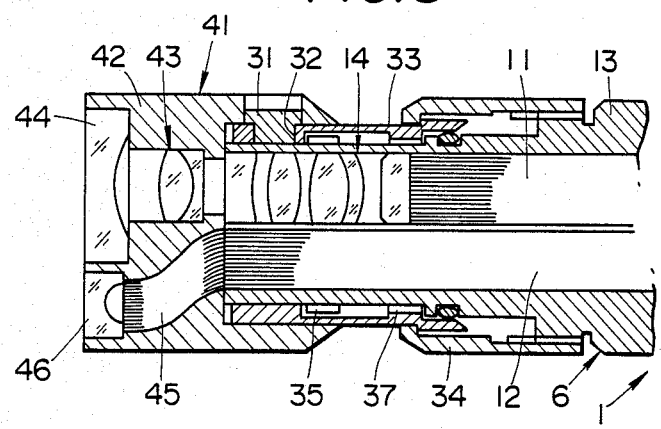
FIG. 5 is a sectioned view showing the second embodiment of the present invention.
Figure 6:
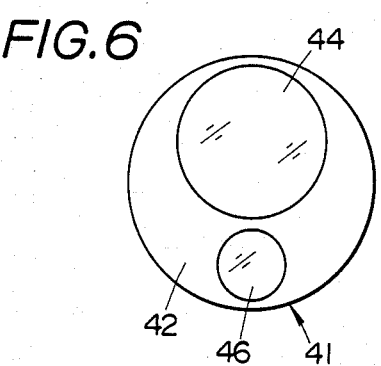
FIG. 6 is an elevation of FIG. 5.

FIG. 5 shows the second embodiment of the present invention.

A tip adaptor 41 of this second embodiment is a straight sight type adaptor for varying the angle of vision.

In this tip adaptor 41, a front adaptor body 42 opposed to the objective system 14 provided in a tip part 6' of an endoscope 1' is provided with a through hole and contains a vision angle varying lens 43 in the through hole. This lens 43 closed in the front part with a concave lens 44 having a function as of a cover glass. A light guide 45 is inserted through a through hole provided as bent on the side reverse to the above mentioned vision angle varying lens 43 from the part opposed to the exit end of the light guide 12 of the endoscope 1' and is closed at the exit end with an illuminating lens 46.

As apparent from FIG. 5, by inclining the light guide 45 toward the side reverse to the vision angle varying lens 43, a large space can be formed in the part opposed to the objective system 14 and the vision angle varying lens 43 of a large caliber is arranged in this space.

In the second embodiment, the adaptor body 42 on the rear end side is the same as in the first embodiment in the structure and connecting method. By the way, the same parts as in the first embodiment are represented by the same reference numerals.

Therefore, according to this second embodiment, the optical system arranging space can be sufficiently secured and therefore a sufficient resolving power can be secured.

The design in the case of containing a lens system of a different angle of vision is so free as to be easy.

Figure 7:
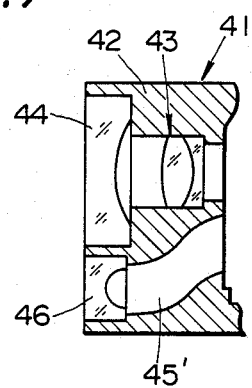
FIG. 7 is a sectioned view showing a part of the third embodiment of the present invention.

FIG. 7 shows the third embodiment of the present invention.

In this third embodiment, a single rod-shaped optical member 45' is used instead of the light guide 45 in the above mentioned second embodiment. This rod-shaped optical member 45' may be provided on the outer peripheral surface with such reflecting member as of aluminum or may be coated on the outer peripheral surface with a member of a low refractive index so that no light may leak in the course of the transmission and can be applied also to the first embodiment.

It is apparent that, in this invention, working modes different in a wide range can be formed on the basis of this invention without deviating from the spirit and scope of the invention. This invention is not restricted by its specific working mode except by ing limited by the appended claims.

What is claimed is:

1. An endoscope tip adaptor removably fitted to an elongate flexible tube of an endoscope, said elongated flexible tube including an image guide and a first light guide therein, said endoscope tip adaptor and said elongated flexible tube having a substantially same diameter and being coaxial, said endoscope tip adaptor, comprising:

a lens means for transmitting an image, said lens means being adapted to fit to said image guide; and
   a second light guide being adapted to fit to said first light guide, wherein the axis of said second light guide is inclined from an axis of said first light guide away from said lens means in order to provide more room in said tip adaptor for said lens means.

2. An endoscope tip adaptor according to claim 1, wherein said second light guide has a curvature of a comparatively large radius so that transmitted through said second light guide a light projects sidewise.

3. An endoscope tip adaptor according to claim 1, wherein the axis of the end of said second light guide is in parallel to the axis of said first light guide.

4. An endoscope tip adaptor according to claim 1, wherein said light guide is formed of a bundle of fibers.

5. An endoscope tip adaptor according to claim 3, wherein said second light guide is formed of a single rod-shaped optical member.

6. An endoscope tip adaptor according to claim 5, wherein said second light guide is provided with a reflecting member such as aluminum on the surface thereof.

7. An endoscope tip adaptor according to claim 5, wherein said second light guide is coated with a material of a low refractive index.

* * * * *